US012667278B2

(12) United States Patent
Mehta et al.

(10) Patent No.: US 12,667,278 B2
(45) Date of Patent: Jun. 30, 2026

(54) POSTURE MONITORING METHOD, POSTURE MONITORING DEVICE, POSTURE ANALYSIS METHOD AND POSTURE ANALYSIS SYSTEM

(71) Applicant: TACNIQ PTE. LTD., Singapore (SG)

(72) Inventors: Aashish Mehta, Singapore (SG); Liang Wei Low, Singapore (SG); Zijun Melvin Chan, Singapore (SG)

(73) Assignee: TACNIQ PTE. LTD., Singapore (SG)

( * ) Notice: Subject to any disclaimer, the term of this patent is extended or adjusted under 35 U.S.C. 154(b) by 36 days.

(21) Appl. No.: 19/097,690

(22) Filed: Apr. 1, 2025

(65) Prior Publication Data

US 2025/0302336 A1 Oct. 2, 2025

(30) Foreign Application Priority Data

Apr. 1, 2024 (SG) ............................ 10202400954V

(51) Int. Cl.
*A61B 5/11* (2006.01)
*G16H 15/00* (2018.01)
(52) U.S. Cl.
CPC ............ *A61B 5/1116* (2013.01); *G16H 15/00* (2018.01); *A61B 2562/0247* (2013.01)
(58) Field of Classification Search
CPC .......... A61B 5/1116; A61B 2562/0247; G16H 15/00
See application file for complete search history.

(56) References Cited

U.S. PATENT DOCUMENTS

| | | | |
|---|---|---|---|
| 2010/0010383 A1* | 1/2010 | Skelton | A61N 1/36132 600/587 |
| 2010/0076358 A1* | 3/2010 | Richardson | A63B 23/0244 602/19 |
| 2012/0245491 A1* | 9/2012 | Amell | A61B 5/6893 600/595 |
| 2012/0265104 A1* | 10/2012 | Menegon | G06V 40/23 600/595 |
| 2014/0266737 A1* | 9/2014 | Caldwell | H04Q 9/00 340/573.7 |
| 2017/0156639 A1 | 6/2017 | Gokhale et al. | |
| 2020/0214622 A1 | 7/2020 | Larson et al. | |

(Continued)

FOREIGN PATENT DOCUMENTS

KR 20180064247 A 6/2018

OTHER PUBLICATIONS

Foreign Communication from a Related Counterpart Application, International Search Report and Written Opinion mailed Jul. 18, 2025, International Application No. PCT/SG2025/050236 filed on Apr. 1, 2025.

*Primary Examiner* — Ryan W Sherwin
(74) *Attorney, Agent, or Firm* — Conley Rose, P.C.

(57) ABSTRACT

Methods, devices and systems for monitoring and analysis posture are described. A posture monitoring method comprises: measuring force sensor data from at least four force sensors positioned on a wearable device; determining pressure distribution data from the force sensor data, the pressure distribution data indicating a distribution of pressure across a lumbar region of a wearer of the wearable device; using a machine learning model system to classify a posture of the wearer; and generating an alert based on the classification of the posture of the wearer.

18 Claims, 5 Drawing Sheets

(56)          References Cited

U.S. PATENT DOCUMENTS

| | | | |
|---|---|---|---|
| 2020/0268589 A1 | 8/2020 | Hoy | |
| 2023/0056977 A1* | 2/2023 | Ishac | A61B 5/1116 |
| 2024/0023647 A1* | 1/2024 | Chung | A61B 5/6805 |
| 2024/0041348 A1 | 2/2024 | Sacks et al. | |
| 2025/0033533 A1* | 1/2025 | Heurlin | B60N 2/0273 |

* cited by examiner

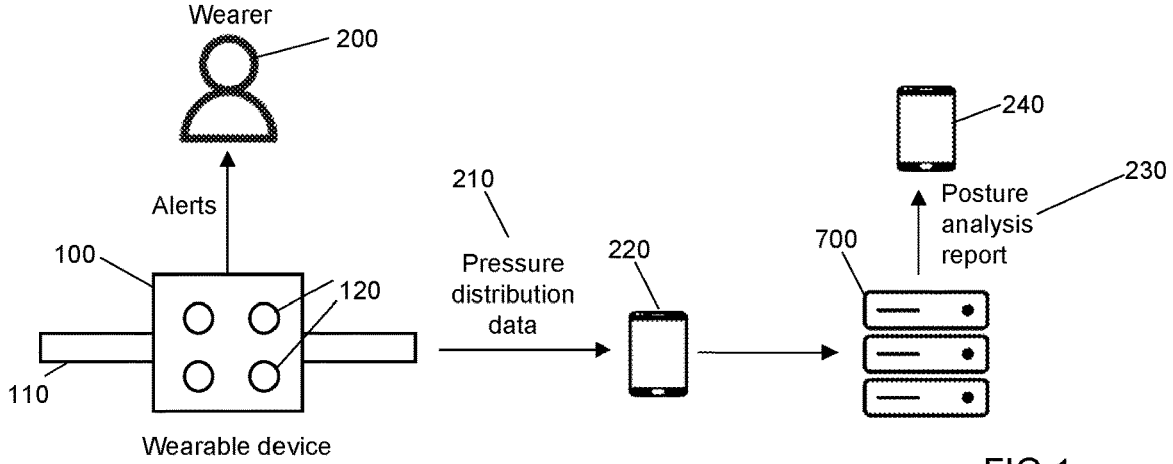
FIG.1
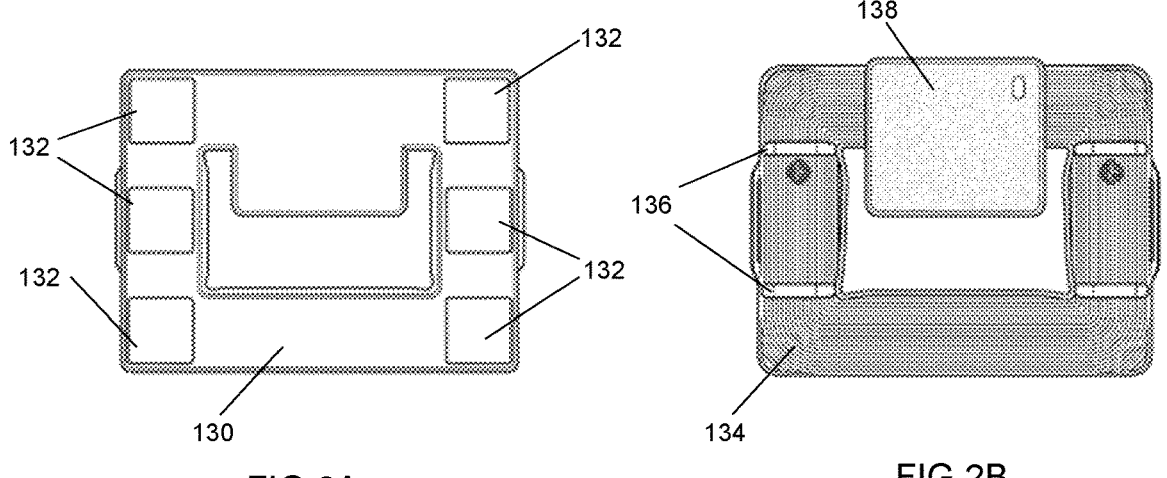
FIG.2A
FIG.2B
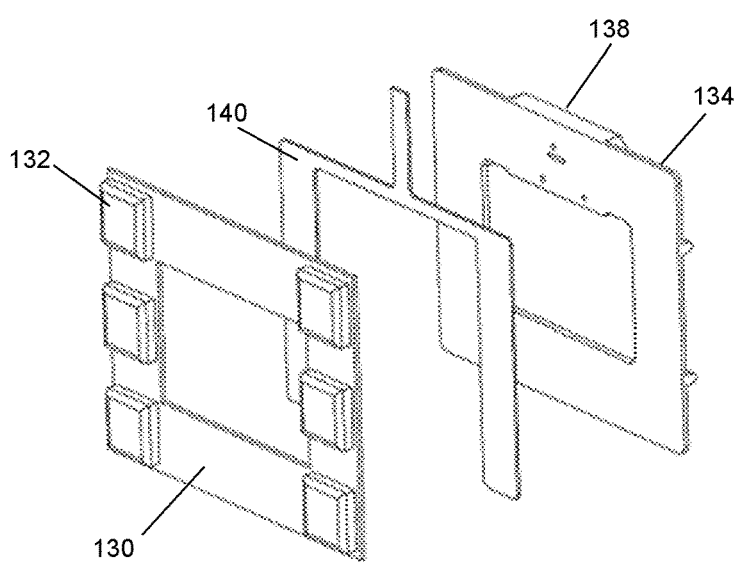
FIG.2C

400

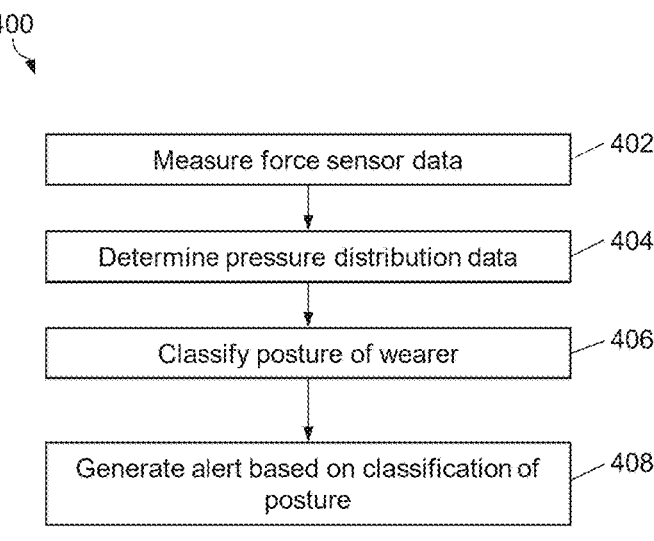

Measure force sensor data — 402

Determine pressure distribution data — 404

Classify posture of wearer — 406

Generate alert based on classification of posture — 408

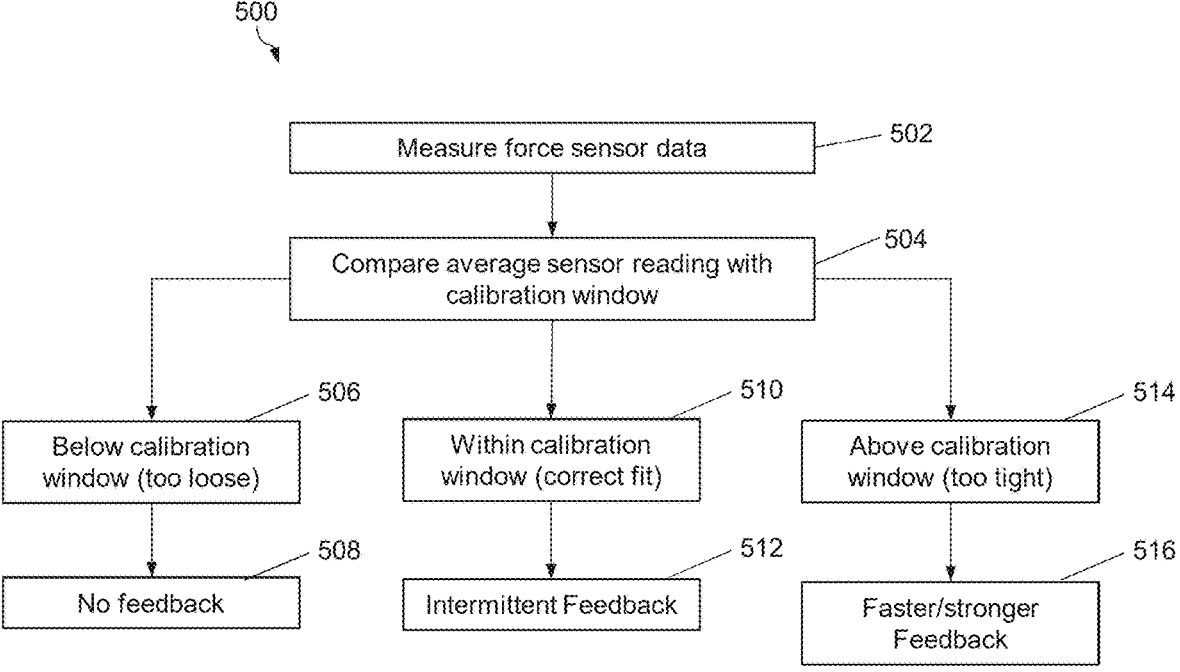

Measure force sensor data — 502

Compare average sensor reading with calibration window — 504

Below calibration window (too loose) — 506

Within calibration window (correct fit) — 510

Above calibration window (too tight) — 514

No feedback — 508

Intermittent Feedback — 512

Faster/stronger Feedback — 516

POSTURE MONITORING METHOD, POSTURE MONITORING DEVICE, POSTURE ANALYSIS METHOD AND POSTURE ANALYSIS SYSTEM

CROSS REFERENCE TO RELATED APPLICATION

The present application claims priority to Singapore App. No. SG10202400954V filed on Apr. 1, 2024 with the Intellectual Property Office of Singapore, the entire disclosure of which is incorporated herein by reference.

TECHNICAL FIELD

The present disclosure relates to posture monitoring and analysis. In particular, the present disclosure relates to the wearable devices and the use of machine learning to monitor and analyze posture.

BACKGROUND

Workplace-related musculoskeletal disorders, particularly back injuries, are among the most common and costly occupational health issues. Industries such as logistics, warehousing, and healthcare rely on manual handling tasks, increasing the risk of chronic injuries due to repetitive stress and improper posture.

Current ergonomic solutions, including motion-tracking wearables and manual assessments, suffer from limitations such as lack of real-time feedback to correct posture dynamically, an inability to quantify and track high-risk movements with precision and limited adaptability to different body types and job roles.

SUMMARY

According to a first aspect of the present disclosure, a posture monitoring method is provided. The method comprises: measuring force sensor data from at least four force sensors positioned on a wearable device; determining pressure distribution data from the force sensor data, the pressure distribution data indicating a distribution of pressure across a lumbar region of a wearer of the wearable device; using a machine learning model system to classify a posture; and generating an alert based on the classification of the posture of the wearer.

The method analyzes movement patterns and detects improper posture in real time. Posture classifications may include Good pickup, Upright, Forward Bend, Backward Bend, Right Twist and Left Twist. The alert may be generated if the posture of the wearer corresponds to a high-risk posture. The alert may continue until the wearer moves to a low-risk posture. The alert may be provided as an audio alert, a visual alert such as a flashing light and/or a vibration alert.

In an embodiment, the machine learning model system comprises a pressure data to posture model trained to classify the posture the wearer from the pressure distribution data.

In an embodiment, the machine learning model system comprises a pressure data to pose model trained to estimate a pose of the wearer of the wearable device and a pose to posture model trained to classify a posture of the wearer based on the estimated pose, and wherein using the machine learning model system to classify a posture of the wearer comprises estimating the pose of the wearer using the pressure data to pose model and classifying the posture of the wearer using the pose to posture model.

The pressure data to pose model may be configured to generate an intermediate representation that encodes information related to the pose of the wearer. The intermediate representation may take various forms, including but not limited to: a set of estimated key skeletal points, a vector representation of the pose, joint angle configurations, kinematic chains, or latent embeddings produced by a neural network. The specific form of the intermediate representation may be selected based on the requirements of the downstream application or processing pipeline.

The pressure distribution data may be determined from the force sensor data using baseline calibration data which may be determined during a calibration period in which the wearer of the wearable device adopts a calibration posture.

The method may comprise, during a device fit calibration period, comparing an average sensor output from the at least four force sensors with a calibration window and generating an indication indicating a result of the comparison.

According to a second aspect of the present disclosure, a wearable device for monitoring posture is provided. The wearable device comprises: a sensor array comprising at least four force sensors arranged to be positioned on a lumbar region of a wearer of the wearable device; a data storage unit storing a machine learning model system configured to classify a posture of the wearer of the wearable device using pressure distribution data indicating a distribution of pressure across the lumbar region of the wearer; a feedback unit configured to generate alerts; and a controller configured to receive force sensor data from the at least four force sensors, determine pressure distribution data from the force sensor data, input the pressure distribution data into the machine learning model system, and to control the feedback unit to generate an alert if the posture of the wearer is classified based on the classification of the posture of the wearer.

In an embodiment, the machine learning model system comprises a pressure data to posture model trained to classify the posture the wearer from the pressure distribution data.

In an embodiment, the machine learning model system comprises a pressure data to key points model trained to estimate a pose of the wearer of the wearable device and a pose to posture model trained to classify a posture of the wearer based on the estimated pose, and wherein using the machine learning model system to classify a posture of the wearer comprises estimating the pose of the wearer using the pressure data to pose model and classifying the posture of the wearer using the pose to posture model.

The wearable device may comprise a belt portion configured to be worn around the waist and being configured to adjust a fit of the wearable device on the wearer, wherein the controller is further configured to compare an average sensor output from the at least four force sensors with a calibration window during a device fit calibration period and to control the feedback unit to generate an indication of a result of the comparison.

The controller may be further configured to determine pressure distribution data from the force sensor data by determining a deviation of the force sensor data from baseline calibration data. In an embodiment, the controller is further configured to determine the baseline calibration data during a sensor calibration period in which the wearer of the wearable device adopts a calibration posture.

The wearable device may further comprise a tilt sensor configured to generate orientation data, wherein the controller is further configured to input the orientation data into the machine learning model system.

The wearable device may further comprise a wireless communication module configured to generate signals indicative of the pressure distribution data and corresponding time stamp data. The signals may be sent to a server for posture analysis of the wearer over a period of time.

According to a third aspect of the present disclosure, a posture analysis method is provided. The posture analysis method comprises: receiving pressure distribution data and corresponding time stamp data, the pressure distribution data indicating a distribution of pressure across a lumbar region of a wearer of a wearable device; using a machine learning model system to classify a posture of the wearer into one of a set of posture types at each of a plurality of times indicated by the time stamp data; and generating a posture analysis report indicating a time spent by the wearer in posture types of the set of posture types.

In an embodiment, the machine learning model system comprises a pressure data to posture model trained to classify the posture the wearer from the pressure distribution data.

In an embodiment, wherein the machine learning model system comprises a pressure data to pose model trained to estimate a pose of the wearer of the wearable device and a pose to posture model trained to classify a posture of the wearer based on the estimated pose, and wherein using the machine learning model system to classify a posture of the wearer comprises estimating the pose of the wearer using the pressure data to pose model and classifying the posture of the wearer using the pose to posture model.

According to a third aspect of the present disclosure, a posture analysis system is provided. The posture analysis system comprises: a processor, a machine learning model storage device storing a machine learning model system and a data storage device storing computer program instructions operable to cause the processor to: receive pressure distribution data and corresponding time stamp data, the pressure distribution data indicating a distribution of pressure across a lumbar region of a wearer of a wearable device; use a machine learning model system to classify a posture of the wearer into one of a set of posture types at each of a plurality of times indicated by the time stamp data; and generate a posture analysis report indicating a time spent by the wearer in posture types of the set of posture types.

In an embodiment, the machine learning model system comprises a pressure data to posture model trained to classify the posture the wearer from the pressure distribution data.

In an embodiment, the machine learning model system comprises a pressure data to pose model trained to estimate a pose of the wearer of the wearable device and a pose to posture model trained to classify a posture of the wearer based on the estimated pose, and wherein using the machine learning model system to classify a posture of the wearer comprises estimating the pose of the wearer using the pressure data to pose model and classifying the posture of the wearer using the pose to posture model.

BRIEF DESCRIPTION OF THE DRAWINGS

In the following, embodiments of the present invention will be described as non-limiting examples with reference to the accompanying drawings in which:

FIG. 1 is a schematic of a system comprising a wearable device and a posture analysis system according to an embodiment of the present invention;

FIG. 2A to FIG. 2D show a wearable device according to an embodiment of the present invention;

FIG. 4 is a flowchart showing a posture monitoring method according to an embodiment of the present invention;

FIG. 5 is a flowchart showing a method of calibrating the fit of a wearable device according to an embodiment of the present invention;

DETAILED DESCRIPTION

Figure 2D:
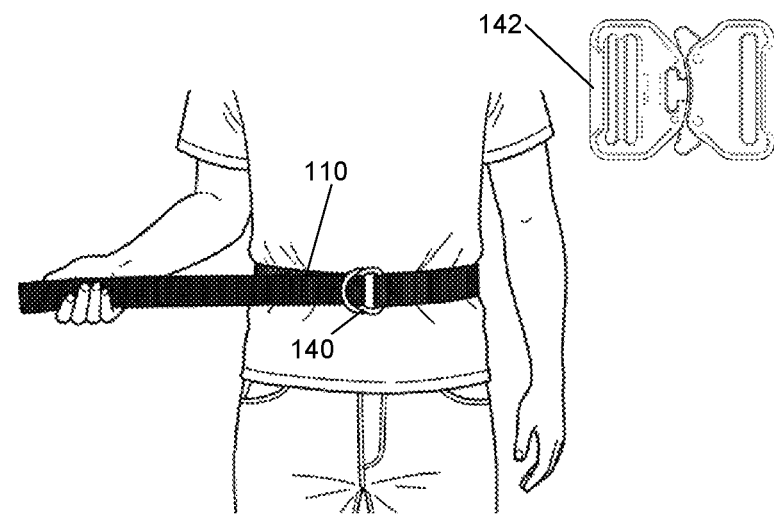

The present disclosure relates to posture monitoring and analysis. As described in more detail below, a wearable device is provided with sensors which allow real-time monitoring of the posture of a wearer of the device and the generation of alerts when the wearer enters a high risk posture. In addition to real-time monitoring, the posture of the wearer may also be analyzed over periods of time.

FIG. 1 is a schematic of a system comprising a wearable device and a posture analysis system according to an embodiment of the present invention. As shown in FIG. 1, a wearable device 100 is provided with a belt portion 110 and can be worn by a wearer 200. When the wearable device 100 is worn by the wearer 200, force sensors 120 arranged on the wearable device 120 measure a pressure distribution on the lower back or lumbar region of the wearer 200. Using the pressure distribution, a machine learning model provided in the wearable device 100 classifies the posture of the wearer. The classification may be to classify the posture as either high-risk or low risk, or may be to classify the posture from among a set of posture types such as good pickup, upright, forward bend, backward bend, right twist and left twist. If the posture is classified as high-risk an alert may be generated to alert the wearer of the high-risk posture. The alert may be, for example, an audio alert, a visual alert or a vibration alert.

The wearable device 100 uses multi-point force sensors to capture real-time pressure, strain, and tilt from the user's back. These sensors are embedded in a flexible yet durable material that conforms to various body types while maintaining high sensitivity to force distribution.

In addition to providing real-time monitoring and alerts, the wearable device 100 may also send pressure distribution data 210 to a communication device 220 such as a smart phone device which in turn sends the pressure distribution data to a posture analysis system 700. The posture analysis system 700 may be implemented as a server or a cloud based system which analyses the posture of the wearer 200 over time and generates posture analysis reports 230. The posture analysis reports 230 may be sent to a user device 240 which may, for viewing, by, for example a supervisor of the wearer 200.

FIG. 2A to FIG. 2D show a wearable device according to an embodiment of the present invention. FIG. 2A shows the front side of the wearable device which faces the lumbar region of the wearer when the device is worn. As shown in FIG. 2A, the front side of the wearable device has a body portion 130 on which 6 sensor pads 132 are formed. The sensor pads 132 are formed from a gel material having a Shore hardness of 0-10. The thickness of the gel pads is 10 mm or more. The body portion 130 is formed from a soft elastomer to allow the wearable device to accommodate different body shapes.

FIG. 2B shows the rear side of the wearable device which faces away from the wearer when the device is worn. As shown in FIG. 2B, the rear side of the wearable device has a body portion 134 on which connectors 136 for the belt portion are arranged. The body portion 134 also comprises a housing 138 which houses control circuitry of the wearable device. The body portion 134 is formed from a plastic material which provides rigidity to ensure accurate pressure readings.

FIG. 2C shows an exploded view of the wearable device. As shown in FIG. 2C, a sensor circuit 140 is provided between the body portion 132 of the front surface and the body portion 134 of the rear surface of the wearable device. The sensor circuit 140 is provided on an IP68 waterproof breathable membrane. The sensor circuit 140 comprises 6 force sensors which are located under the gel pads 132 on the front surface of the wearable device.

FIG. 2D shows the adjustment of the belt portion of the wearable device. As shown in FIG. 2D, the belt portion 110 of the wearable device is provided with an adjustable fastener. The adjustable fastener may be a double ring 140 or friction buckle 142. The adjustment allows the pressure on the sensor array to be calibrated. The calibration process is described in more detail below with reference to FIG. 5.

Figure 3:
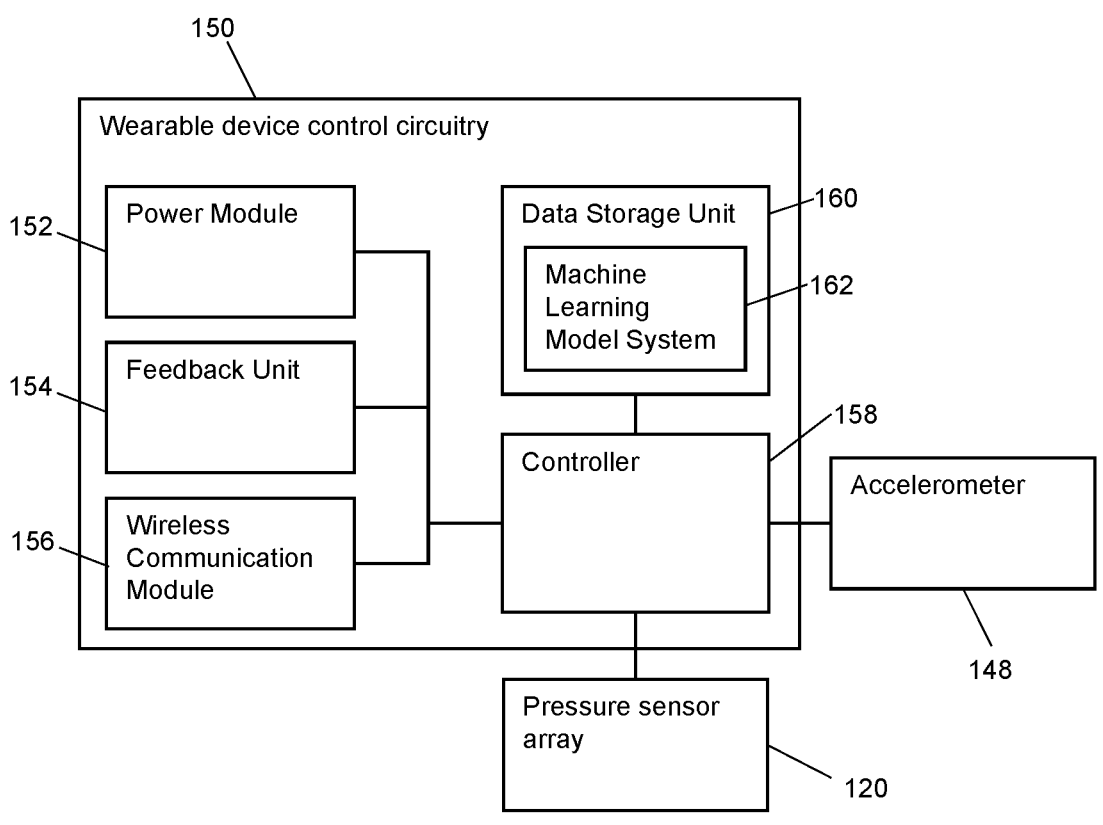
FIG. 3 is a block diagram showing control circuitry of a wearable device according to an embodiment the present invention.

FIG. 3 is a block diagram showing control circuitry of a wearable device according to an embodiment the present invention. As shown in FIG. 3, the wearable device control circuitry 150 comprises a power module 152, a feedback unit 154, a wireless communication module 156, a controller 158 and a data storage unit 160. The power module 152 comprises a battery which supplies power to the wearable device. The feedback unit 154 may comprise an actuator to provide vibration feedback, a speaker or buzzer to provide audio feedback, a light or group of lights to provide visual feedback or a combination feedback types. The wireless communication module 156 may be Bluetooth or WiFi module which allows the wireless device to send and receive data wirelessly, for example to send pressure distribution data to the posture analysis system 700 shown in FIG. 1. The data storage unit 160 stores a machine learning system 162. The machine learning system 162 is configured to classify the posture of the wearer of the wearable device based on the pressure distribution data. In some embodiments, accelerometer data or orientation data is also input into the machine learning model system 162 to classify the posture of the wearer of the wearable device. The controller 158 is a microcontroller or system on a chip (SoC) which performs processing and controls the wireless communication module 156 and feedback unit 154. The controller 158 is also connected to the pressure sensor array 120 and an accelerometer 148. The pressure sensor array 120 may provided as an array of piezoelectric force sensors. In some embodiment, the pressure sensor array comprises 6 sensors in a 3×2 array with two vertical rows of three sensors arranged on the lumbar region of the wearer. In other embodiments, fewer or more sensors may be provided. In order to provide an array map of back pressure distribution on the wearer, at least four sensors are required, for example in a 2×2 array. Increasing the number of sensors in the array may increase the accuracy of posture classification.

FIG. 4 is a flowchart showing a posture monitoring method according to an embodiment of the present invention. The method 400 shown in FIG. 4 is carried out by the wearable device control circuitry 150 shown in FIG. 3. The method shown in FIG. 4 may be repeated continuously, for example at a frequency of 100 Hz.

In step 402, the pressure sensor array 120 measures force sensor data which is indicative of the forces on each of the force sensors. The force sensor data is received by the controller 158.

In step 404, the controller 158 determines pressure distribution data from the force sensor data. The pressure distribution data may be determined from the force sensor data by determining a deviation from baseline calibration force data and multiplying by a predetermined constant. The calibration period may take place after the wearer puts on the wearable device and the wearer may be directed to adopt a calibration posture for a calibration period.

In step 406, the pressure distribution data is input into machine learning model system 162 by the controller 158. The machine learning model system 162 classifies the posture of the wearer. The classification of the posture of the wearer may be into one of a set of classification or may be a classification as high-risk or low-risk.

In step 408, the controller 158 controls the feedback unit 154 to generate an alert based on the classification of the posture of the wearer. For example, the alert may be generated if the posture of the wearer is classified as high risk. The alert may be generated as haptic, sound and/or light.

A de-calibration process may be implemented as follows. If, after calibration, the average sensor values drop below a defined threshold and remain below that threshold for a specified period, the device automatically de-calibrates. Upon de-calibration, the device produces a brief vibration and plays a calibration tone to alert the user that the calibration state has been reset, prompting a re-calibration if necessary.

FIG. 5 is a flowchart showing a method of calibrating the fit of a wearable device according to an embodiment of the present invention. The method 500 shown in FIG. 5 is carried out by the wearable device control circuitry 150 shown in FIG. 3. The method 500 is carried out when the wearer puts on the wearable device and is carried out to calibrate the fit of the wearable device. For example, after the user puts on the device, they may be instructed to adjust the device to a predefined tightness while adopting a specific calibration posture.

The wearer puts on the wearable device and following the wearer putting on the wearable device, in step 502, the pressure sensor array 120 measures force sensor data which is indicative of the forces on each of the force sensors. The force sensor data is received by the controller 158.

In step 504, the controller 158 calculates an average sensor reading and compares the average sensor reading with a calibration window. The calibration window indicates a range of force sensor readings. The method 500 moves to step 506 if the average sensor reading is below the calibration window. This would occur if the belt of the wearable device is too loose. The method then moves to step 508 and in this example no feedback is given which indicates that the fit is too loose. If the average sensor reading is within the calibration window, the method moves to step 510, and then to step 512 in which intermittent feedback is given to the wearer to indicate that the fit is correct. If the average sensor reading is above the calibration window, the method moves to step 514, and then to step 516 in which stronger or faster feedback is given to the wearer to indicate that the fit is too tight. It will be appreciated that the feedback shown in FIG. 5 is one example and other types of feedback may be given for the three results of the comparison of the average sensor reading with the calibration window.

Once the average sensor value remains within the calibration window for a set period (e.g., 3 seconds), the device: provides confirmation feedback via a brief vibration and a calibration tone and captures and stores the sensor values at that moment as baseline calibration data (baseline force readings) for subsequent posture monitoring.

As described above, feedback is given to the wearer to indicate whether the fit is in the correct range and if the fit is outside the correct range, the wearer can adjust the fit using the adjustable fastener shown in FIG. 2D.

Figure 6:
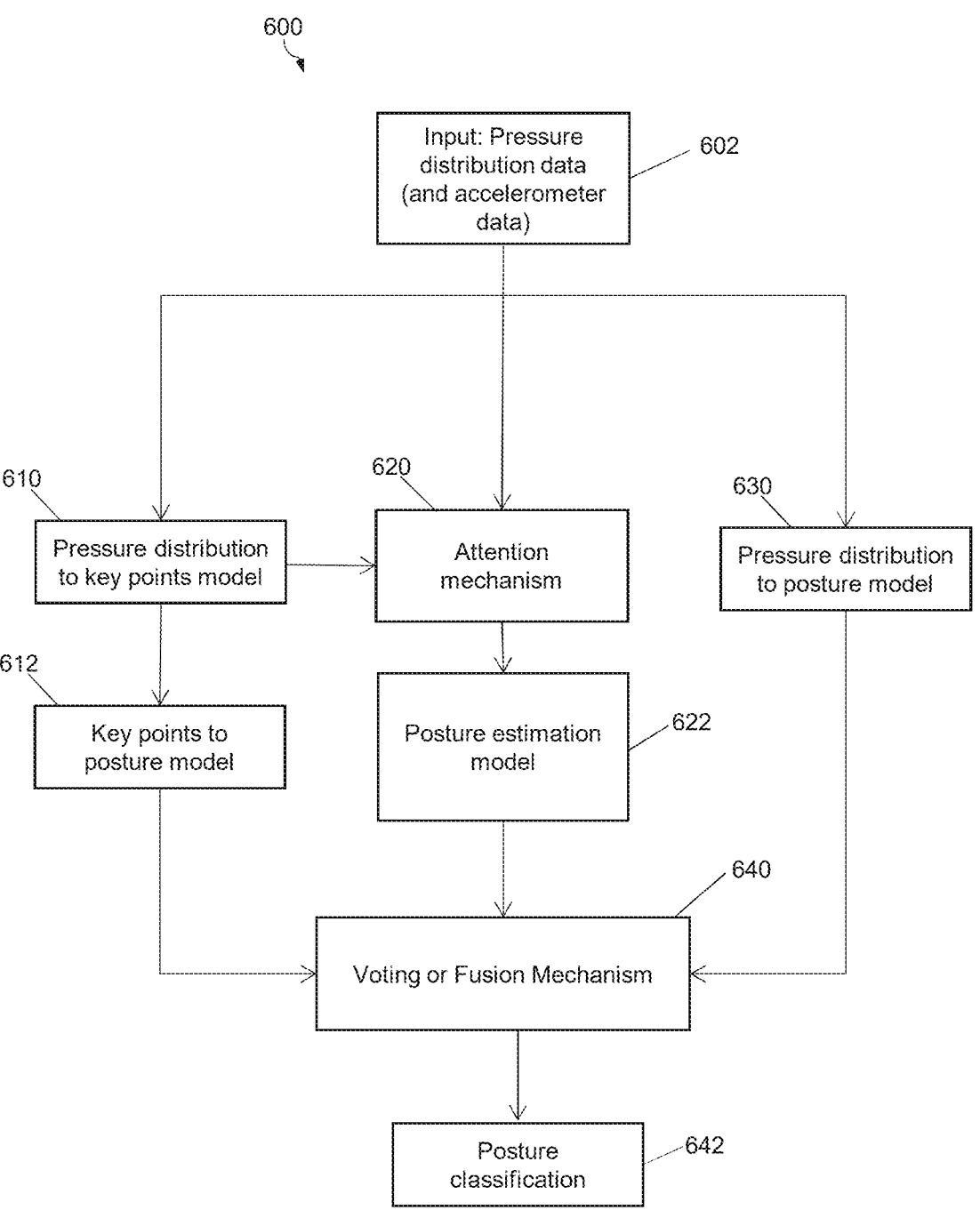
FIG. 6 is a block diagram showing a machine learning system in a wearable device or a posture analysis system according to an embodiment of the present invention.

Prior to calibration, the controller may continuously sample force sensor data and maintains a sliding window of these values. Then during the calibration/tightness determination phase, the average value of the sensor data within this window is computed in real time to evaluate the device's tightness. When the device remains within the calibration range for a set duration (e.g., 3 seconds), the controller captures the average sensor values from the final state of the window as the calibration baseline. Once calibrated, the controller increases the sampling rate (e.g., to 100 Hz) for enhanced precision in monitoring. The controller continuously calculates the average of the real-time sensor data and compares it against the stored calibration baseline multiplied by a predetermined constant (derived from extensive testing). This comparison determines different postures or pressure distribution states, thereby triggering the appropriate feedback FIG. 6 is a block diagram showing a machine learning model system in a wearable device or a posture analysis system according to an embodiment of the present invention. The machine learning system 600 may correspond to the machine learning model system 162 shown in FIG. 3 or the machine learning model system 732 shown in FIG. 7.

As shown in FIG. 6, the machine learning model system 600 takes pressure distribution data 602 as input. The pressure distribution data 602 indicates the In some embodiments, the input also comprises accelerometer data.

The pressure distribution data 602 is input into three machine learning models.

A pressure distribution to key points model 610 is trained to convert pressure distribution data into estimated skeletal key points of the wearer. The output from the pressure distribution to key points model 610 is fed into a key points to posture model 612 which classifies posture based on the extracted skeletal key points.

A posture prediction model 622 is trained on both key point data and pressure distribution data (and may also be trained on accelerometer data). The input to the posture prediction model 622 may be fed into an attention mechanism 620 which refines predictions by prioritizing the most relevant input data, for example by prioritizing particularly relevant regions in the pressure sensor data. The attention mechanism 620 enhances model accuracy by integrating both key points and tactile data features. The attention mechanism 620 uses an attention-based AI mechanism to weigh significant pressure distribution and key point features.

A pressure distribution to posture model 630 is trained to directly map pressure distribution data onto posture classification.

The outputs from the three models (the key points to posture model 612, the posture estimation model 622 and the pressure distribution model 630) are fed into a voting or fusion mechanism which uses ensemble techniques, including voting or fusion-based decision-making, to finalize posture classification. This enhances reliability by aggregating multiple machine learning model outputs.

The final output of the machine learning model system 600 is a posture classification. This classification may be a classification into one of a set of pre-defined categories (for example forward bend, backward bend, twisting, proper lift, upright, etc.). Alternatively, the classification output may be a classification as a high-risk posture or a non-high risk posture. The output posture classification 642 supports both real-time and post-analysis applications for ergonomic assessment.

The pressure distribution to posture model 630 bypasses key point extraction and directly predicts posture from pressure sensor data. It is trained using: Paired datasets of pressure sensor readings and corresponding labeled postures. The wearable device collects data either wirelessly in real-time or from stored sensor data, enabling a robust training process through supervised learning. The model is trained on real-world movement data, focusing on key postures such as Upright, Forward Bend, Backward Bend, Right Twist & Left Twist), ensuring it learns posture patterns purely from pressure sensor data inputs without relying on external motion capture or visual data. This pathway allows fast and efficient posture classification without requiring intermediate skeletal mapping.

The pressure distribution to key points model 610 provides for a more structured understanding of movement. The model 610 is trained using: pressure sensor data aligned with motion capture outputs. Human body key points extracted from video analytics (e.g., OpenPose, OpenMM). By learning the correlation between pressure distribution and skeletal movement, the model estimates key points purely from pressure sensor data input.

The key points to posture model 612 classifies postures based on estimated skeletal key points. Training includes: Video-based movement recordings paired with key point extractions and manual labeling of posture categories. This approach allows a structured, pose-driven classification of posture, independent of direct pressure sensor inputs.

The posture estimation model 622 takes both key point data and pressure distribution data as inputs. To refine predictions, the attention mechanism 620 is employed to Identify key pressure regions that contribute most to posture classification, reduces noise from less informative sensor inputs and enhance accuracy by dynamically adjusting focus on high-impact pressure points.

While FIG. 6 shows three processing pipelines to obtain the final posture classification, in some embodiments a smaller number of processing pipelines may be used. For example, embodiments may be implemented with only the pressure distribution to posture model. Such a configuration would reduce the processing requirements, but may have less accuracy and generalization ability. It has been found that using a two-step model (pressure data to key points followed by key points to posture classification) enables better generalization across different body types, movements, and sensor variations, making the system more robust and scalable. The two-step model may be implemented as a pressure data to pose model which generates an intermediate representation that encodes information related to the pose of the wearer. The intermediate representation may take various forms, including but not limited to: a set of estimated key skeletal points, a vector representation of the pose, joint angle configurations, kinematic chains, or latent embeddings produced by a neural network. The specific form of the intermediate representation may be selected based on the requirements of the downstream application or processing pipeline.

Figure 7:
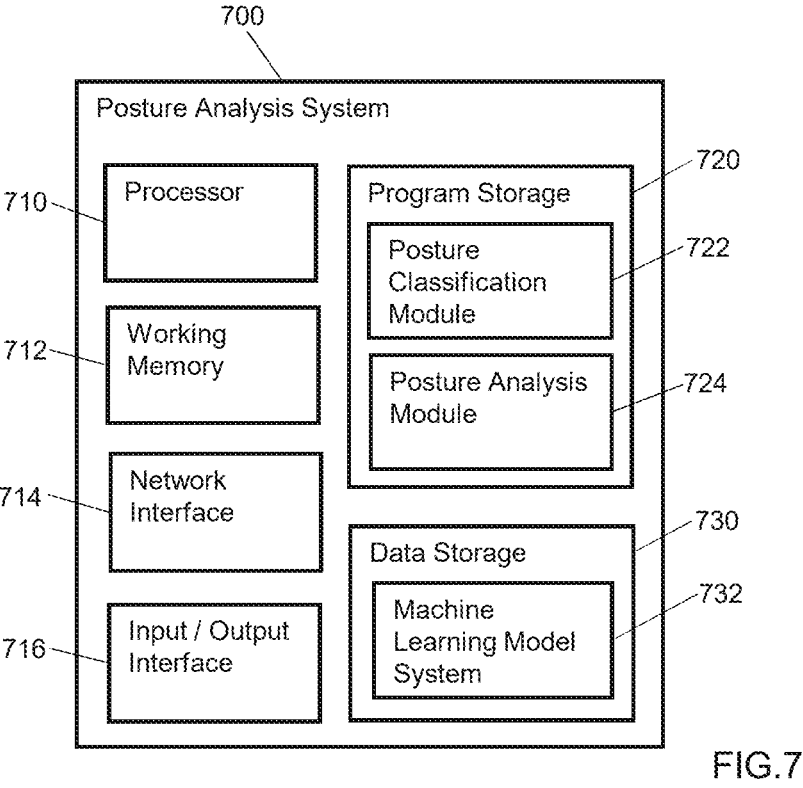
FIG. 7 is a block diagram showing a posture analysis system according to an embodiment of the present invention.

FIG. 7 is a block diagram showing a posture analysis system according to an embodiment of the present invention. The posture analysis system 700 comprises a processor 710, a working memory 712, a network interface 714, an input/output interface 716, program storage 720, and data storage 730. The processor 110 may be implemented as one or more central processing unit (CPU) chips. The program storage 120 is a non-volatile storage device such as a hard disk drive which stores computer program modules. The computer program modules are loaded into the working memory 712 for execution by the processor 710. The data storage 730 is a non-volatile storage device which stores data which is used by the posture analysis system 700 during processing. The data storage 730 may be implemented as a number of separate data storage devices. These devices may physically form part of the posture analysis system 700 or may be separate systems such as servers which communicate with the posture analysis system 700 to provide data when required. The network interface 714 is an interface that allows the posture analysis system 700 to communicate with other devices and receive signals from the wearable device 100. The input/output interface 716 allows a user to input data or commands which are processed by the posture analysis system 700. The input/output interface 716 also allows the results of processing by the posture analysis system 700 to be output to the user. The input/output interface 716 may be implemented as an input device such as a keyboard, pointing device or touch screen and an output device such as a display or a printer.

The program storage 720 stores a posture classification module 722, and a posture analysis module 724. The computer program modules cause the processor 710 to execute various processing methods which are described in more detail below. The program storage 720 may be referred to in some contexts as computer readable storage media and/or non-transitory computer readable media. As depicted in FIG. 7, the computer program modules are distinct modules which perform respective functions implemented by the posture analysis system 700. It will be appreciated that the boundaries between these modules are exemplary only, and that alternative embodiments may merge modules or impose an alternative decomposition of functionality of modules. For example, the modules discussed herein may be decomposed into sub-modules to be executed as multiple computer processes, and, optionally, on multiple computers. Moreover, alternative embodiments may combine multiple instances of a particular module or sub-module. It will also be appreciated that, while a software implementation of the computer program modules is described herein, these may alternatively be implemented as one or more hardware modules (such as field-programmable gate array(s) or application-specific integrated circuit(s)) comprising circuitry which implements equivalent functionality to that implemented in software.

Although the posture analysis system 700 is described with reference to a computer, it should be appreciated that the posture analysis system 700 may be formed by two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the posture analysis system 700 to provide the functionality of a number of servers that is not directly bound to the number of computers in the posture analysis system 700. In an embodiment, the functionality disclosed above may be provided by executing the application and/or applications in a cloud computing environment. Cloud computing may comprise providing computing services via a network connection using dynamically scalable computing resources. A cloud computing environment may be established by an enterprise and/or may be hired on an as-needed basis from a third party provider.

The data storage 730 stores a machine learning model system 732. The machine learning model system 732 may correspond to the machine learning model system 600 described above with reference to FIG. 6.

Figure 8:
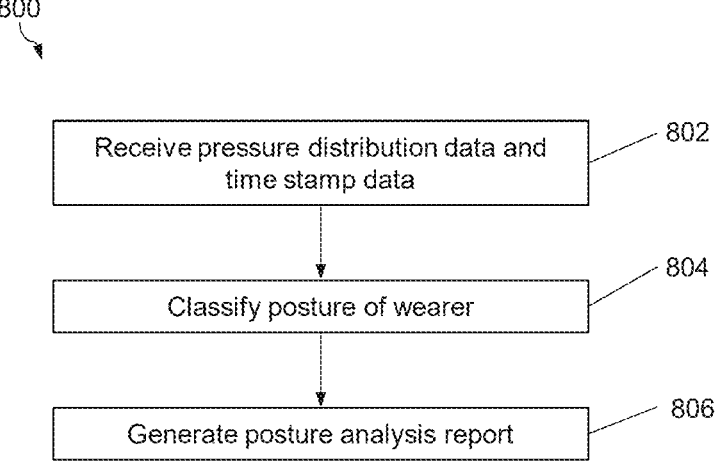
FIG. 8 is a flowchart showing a posture analysis method according to an embodiment of the present invention.

FIG. 8 is a flow chart showing a posture analysis method according to an embodiment of the present invention. The method 800 shown in FIG. 8 is carried out by the posture analysis system 700 shown in FIG. 7.

In step 802, the posture analysis system 700 receives pressure distribution data and time stamp data. The pressure distribution data and time stamp data may be received from a wearable device such as that shown in FIG. 1. As shown in FIG. 1, the data may be transmitted from the wearable device to a communication device before being transmitted from the communication device to the posture analysis system 700.

In step 804, the processor 710 of the posture analysis system 700 executes the posture classification module 722 to classify the posture of the wearer of the wearable device. As discussed above, the machine learning model system 732 is trained to classify the posture of the wearer based on pressure distribution data as input.

In step 806, the processor 710 of the posture analysis system 700 executes the posture analysis module 724 to generate a posture analysis report. The posture analysis report may indicate the postures of the wearer and the time the wearer has spent in each posture.

As described above, the present disclosure provides a wearable device for monitoring of posture of a wearer. The functionality of the device may be integrated into safety vests, belts, or back braces. The Multi-point force sensors capture real-time pressure and strain. Flexible & rigid sensing adapts to various body types. Optimized materials (0-10 Shore A gel hardness, 10 mm+ thickness) enhance sensing accuracy. The wearable device may have breathable design with perforations enables IP68 rating for durability and comfort. The calibration stage ensures accurate adjustments for various body sizes and shapes.

Whilst the foregoing description has described exemplary embodiments, it will be understood by those skilled in the art that many variations of the embodiments can be made within the scope and spirit of the present invention.

The invention claimed is:

1. A posture monitoring method comprising:
   measuring force sensor data from at least four force sensors positioned on a wearable device;
   determining pressure distribution data from the force sensor data, the pressure distribution data indicating a distribution of pressure across a lumbar region of a wearer of the wearable device;
   using a machine learning model system to classify a posture of the wearer, wherein the machine learning model system comprises a pressure data to pose model trained to estimate a pose of the wearer of the wearable device and a pose to posture model trained to classify a posture of the wearer based on the estimated pose, and wherein using the machine learning model system to classify a posture of the wearer comprises estimating the pose of the wearer using the pressure data to pose model and classifying the posture of the wearer using the pose to posture model; and generating an alert based on the classification of the posture of the wearer.

2. The posture monitoring method according to claim 1, wherein the machine learning model system comprises a pressure data to posture model trained to classify the posture of the wearer from the pressure distribution data.

3. The posture monitoring method according to claim 1, wherein determining pressure distribution data from the force sensor data comprises determining a deviation of the force sensor data from baseline calibration data.

4. The posture monitoring method according to claim 3, further comprising determining the baseline calibration data during a sensor calibration period in which the wearer of the wearable device adopts a calibration posture.

5. The posture monitoring method according to claim 1, further comprising, during a device fit calibration period, comparing an average sensor output from the at least four force sensors with a calibration window and generating an indication indicating a result of the comparison.

6. A wearable device for monitoring posture, the wearable device comprising:

a sensor array comprising at least four force sensors arranged to be positioned on a lumbar region of a wearer of the wearable device;

a data storage unit storing a machine learning model system configured to classify a posture of the wearer of the wearable device using pressure distribution data indicating a distribution of pressure across the lumbar region of the wearer, wherein the machine learning model system comprises a pressure data to pose model trained to estimate a pose of the wearer of the wearable device and a pose to posture model trained to classify a posture of the wearer based on the estimated pose, and wherein using the machine learning model system to classify a posture of the wearer comprises estimating the pose of the wearer using the pressure data to pose model and classifying the posture of the wearer using the pose to posture model;

a feedback unit configured to generate alerts; and a controller configured to receive force sensor data from the at least four force sensors, determine pressure distribution data from the force sensor data, input the pressure distribution data into the machine learning model system, and to control the feedback unit to generate an alert based on the classification of the posture of the wearer.

7. The wearable device according to claim 6, wherein the machine learning model system comprises a pressure data to posture model trained to classify the posture of the wearer from the pressure distribution data.

8. The wearable device according to claim 6, further comprising a belt portion configured to be worn around a waist and being configured to adjust a fit of the wearable device on the wearer, wherein the controller is further configured to compare an average sensor output from the at least four force sensors with a calibration window during a device fit calibration period and to control the feedback unit to generate an indication of a result of the comparison.

9. The wearable device according to claim 6, wherein the controller is further configured to determine pressure distribution data from the force sensor data by determining a deviation of the force sensor data from baseline calibration data.

10. The wearable device according to claim 9, wherein the controller is further configured to determine the baseline calibration data during a sensor calibration period in which the wearer of the wearable device adopts a calibration posture.

11. The wearable device according to claim 6, further comprising a tilt sensor configured to generate orientation data, wherein the controller is further configured to input the orientation data into the machine learning model system.

12. The wearable device according to claim 6, further comprising a wireless communication module configured to generate signals indicative of the pressure distribution data and corresponding time stamp data.

13. A posture analysis method comprising:

receiving pressure distribution data and corresponding time stamp data, the pressure distribution data indicating a distribution of pressure across a lumbar region of a wearer of a wearable device;

using a machine learning model system to classify a posture of the wearer into one of a set of posture types at each of a plurality of times indicated by the time stamp data, wherein the machine learning model system comprises a pressure data to pose model trained to estimate a pose of the wearer of the wearable device and a pose to posture model trained to classify a posture of the wearer based on the estimated pose, and wherein using the machine learning model system to classify a posture of the wearer comprises estimating the pose of the wearer using the pressure data to pose model and classifying the posture of the wearer using the pose to posture model; and generating a posture analysis report indicating a time spent by the wearer in posture types of the set of posture types.

14. The posture analysis method according to claim 13, wherein the machine learning model system comprises a pressure data to posture model trained to classify the posture of the wearer from the pressure distribution data.

15. A posture analysis system comprising: a processor, a machine learning model storage device storing a machine learning model system and a data storage device storing computer program instructions operable to cause the processor to:

receive pressure distribution data and corresponding time stamp data, the pressure distribution data indicating a distribution of pressure across a lumbar region of a wearer of a wearable device;

use a machine learning model system to classify a posture of the wearer into one of a set of posture types at each of a plurality of times indicated by the time stamp data, wherein the machine learning model system comprises a pressure data to key points model trained to estimate a position of key points of the wearer of the wearable device and a key points to posture model trained to classify a posture of the wearer based on the estimated key points, and wherein using the machine learning model system to classify a posture of the wearer comprises estimating the position of key points of the wearer using the pressure data to key points model and classifying the posture of the wearer using the key points to posture model; and generate a posture analysis report indicating a time spent by the wearer in posture types of the set of posture types.

16. The posture analysis system according to claim 15, wherein the machine learning model system comprises a pressure data to posture model trained to classify the posture the wearer as high-risk or low-risk from the pressure distribution data.

17. A posture monitoring method comprising:

measuring force sensor data from at least four force sensors positioned on a wearable device;

during a device fit calibration period, comparing an average sensor output from the at least four force sensors with a calibration window and generating an indication indicating a result of the comparison;

determining pressure distribution data from the force sensor data, the pressure distribution data indicating a distribution of pressure across a lumbar region of a wearer of the wearable device;

using a machine learning model system to classify a posture of the wearer; and generating an alert based on the classification of the posture of the wearer.

18. A wearable device for monitoring posture, the wearable device comprising:

a sensor array comprising at least four force sensors arranged to be positioned on a lumbar region of a wearer of the wearable device;

a data storage unit storing a machine learning model system configured to classify a posture of the wearer of the wearable device using pressure distribution data indicating a distribution of pressure across the lumbar region of the wearer;

a feedback unit configured to generate alerts; a controller configured to receive force sensor data from the at least four force sensors, determine pressure distribution data from the force sensor data, input the pressure distribution data into the machine learning model system, and to control the feedback unit to generate an alert based on the classification of the posture of the wearer; and a belt portion configured to be worn around a waist and being configured to adjust a fit of the wearable device on the wearer, wherein the controller is further configured to compare an average sensor output from the at least four force sensors with a calibration window during a device fit calibration period and to control the feedback unit to generate an indication of a result of the comparison.

* * * * *